(12) United States Patent
Smith et al.

(10) Patent No.: US 6,624,202 B2
(45) Date of Patent: Sep. 23, 2003

(54) INHIBITORS OF COPPER-CONTAINING AMINE OXIDASES

(75) Inventors: David John Smith, Naantali (FI); Markku Jalkanen, Piispanristi (FI); Ferenc Fülöp, Szeged (HU); László Lázár, Szeged (HU); Zsolt Szakonyi, Szeged (HU); Gábor Bernáth, Szeged (HU)

(73) Assignee: Biotie Therapies Corp., Turku (FI)

( * ) Notice: Subject to any disclaimer, the term of this patent is extended or adjusted under 35 U.S.C. 154(b) by 0 days.

(21) Appl. No.: 09/898,003

(22) Filed: Jul. 5, 2001

(65) Prior Publication Data

US 2002/0173521 A1 Nov. 21, 2002

Related U.S. Application Data

(60) Provisional application No. 60/216,341, filed on Jul. 5, 2000.

(51) Int. Cl.$^7$ .............................................. A61K 31/15
(52) U.S. Cl. ........................ 514/664; 514/642; 514/643
(58) Field of Search ................................ 514/664, 642, 514/643

(56) References Cited

U.S. PATENT DOCUMENTS 3,377,345 A    4/1968   Trepanier et al. ............ 260/244

FOREIGN PATENT DOCUMENTS

WO    WO 93/23023 A1    11/1993
WO    WO 02/02090 A3    1/2002

OTHER PUBLICATIONS

Hoogenboom, L. A. P. et al., "Use of pig hepatocytes to study the inhibition of monoamine oxidase by furazolidone", abstract of Food Chem. Toxicol 29(3), pp. 185–191, 1991.*

CAplus, Accession No. 1968:426896, CAplus English language abstract for Grifantini, M. et al., "Derivatives of N–amino–1–ephedrine and N–amino–d–pseudoephedrine having antidepressive activity," *Il Farmaco Ed. Sci.* 23:197–203, Il Farmaco (1968) (Document AS1 cited in Applicants' IDS filed Jan. 24, 2002).

CAplus, Accession No. 1968:78260, CAplus English language abstract for Ioffe, B.V., and Potekhin, A.A., "New type of ring–chain tautomerism and the simplest tetrahydro–1,3,4–oxadiazine derivatives," *Tetrahedron Lett.* 36:3505–3508, Pergamon Press, Ltd. (1967) (Document AS5).

CAplus, Accession No. 1982:142348, Caplus English language abstract for Takahashi, H., et al., "Synthesis of N–alkylaminoephedrines and their effect on bronchial musculature," *Yakugaku Zasshi* 101:1154–1156, Pharmaceutical Society of Japan (1981) (Document AT4 cited in Applicants' IDS filed Jan. 24, 2002).

Potekhin, A.A., and Bogan'kova, E.A., "Ring–chain Tautomerism of Substituted Hydrazones VII. Substituted 4–tert– butylperhydro–1,3,4–oxadiazines," *Chemistry of Heterocyclic CompouNnds* 9:1321–1326, Plenum Publishing Corporation (1973).

Schmitz, E., et al., "Versuche zur N–Aminierung von Alkaloiden," *Liebigs Ann. Chem.* 1043–1046, Verlag Chemie GmbH (1983).

Trepanier, D.L., et al., "Synthesis and Pharmacological Evaluation of Some Tetrahydrooxadiazinones and Some Dihydroaminooxadiazines," *J. Med. Chem.* 11:357–360, Mack Printing Company (1968).

(List continued on next page.)

*Primary Examiner*—Dwayne C. Jones
(74) *Attorney, Agent, or Firm*—Sterne, Kessler, Goldstein & Fox PLLC

(57) ABSTRACT

The present invention is directed to hydrazino compounds that function as inhibitors of copper-containing amine oxidases commonly known as semicarbazide-sensitive amine oxidases (SSAO), including the human SSAO known as Vascular Adhesion Protein-1 (VAP-1). These SSAO inhibitors have therapeutic utility as drugs to treat conditions and diseases including, but not limited to, a number of inflammatory conditions and diseases (in particular chronic inflammatory conditions such as chronic arthritis, inflammatory bowel diseases, and chronic skin dermatoses), diseases related to carbohydrate metabolism and to aberrations in adipocyte differentiation or function and smooth muscle cell function, and vascular diseases. The compounds have the general formula:

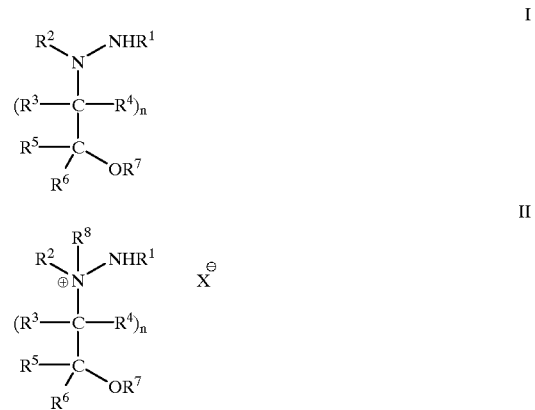

or a pharmaceutically acceptable solvate, hydrate, or salt thereof, wherein $R^1$ to $R^8$ and X are as defined herein.

15 Claims, 1 Drawing Sheet

OTHER PUBLICATIONS

Graser, G., et al., "Incorporation of chirally deuterated putrescines into Pyrrolizidine Alkaloids: A Reinvestigation," *Phytochemistry* 47:1017–1024, Elsevier Science, Ltd. (1998).

Ioffe, B.V., and Potekhin, A.A., "Uber eine neue art von ring–ketten–tautomerie und die einfachsten tetrahydro–1,3, 4–oxadiazinderivate," *Tetrahedron Lett.* 36:3505–3508, Pergamon Press, Ltd. (1967).

Potekhin, A.A., and Zaitsev, B.D., "Ring–chain Tautomerism of Substituted Hydrazones II. Derivatives of 1–hydrazino– and 1–(N–alkylhydrazino)–2–propanols," *Chemistry of Heterocyclic Compounds* 7:277–283, Plenum Publishing Corporation (1971).

Arvilommi, A.–M., et al., "Lymphocyte binding to vascular endothelium in inflamed skin revisited: a central role for vascular adhesion protein–1 (VAP–1)," *Eur. J Immunol.* 26:825–833, VCH Verlagsgesellschaft mbH (1996).

Grifantini, M., et al., "Derivati Delle N–Ammino–1–Efedrina E N–Ammino–d–Pseudoefedrina Ad Attivita Antidepressiva," *Il Farmaco Ed. Sci.* 23: 197–203, Il Farmaco (1968).

Lizcano, J.M., et al., "Inhibition of Bovine Lung Semicarbazide–Sensitive Amine Oxidase (SSAO) by Some Hydrazine Derivatives," *Biochem. Pharmacol.* 52:187–195, Elsevier Science (1996).

Lyles, G.A., "Mammalian Plasma and Tissue–bound Semicarbazide–sensitive Amine Oxidases: Biochemical, Pharmacological and Toxicological Aspects," *Int. J. Biochem. Cell Biol.* 28:259–274, Pergamon Press (1996).

Salmi, M. and Jalkanen, S., "A 90–Kilodalton Endothelial Cell Molecule Mediating Lymphocyte Binding in Humans," *Science* 257:1407–1409, American Association for the Advancement of Science (1992).

Salmi, M. and Jalkanen, S., "Human Vascular Adhesion Protein 1 (Vap–1) Is a Unique Sialoglycoprotein that Mediates Carbohydrate–dependent Binding of Lymphocytes to Endothelial Cells," *J. Exp. Med.* 183:569–579, Rockefeller University Press (1996).

Salmi, M., et al., "Induction and Function of Vascular Adhesion Protein–1 at Sites of Inflammation," *J. Exp. Med.* 178:2255–2260, Rockefeller University Press (1993).

Salmi, M., et al., "Homing of Mucosal Leukocytes to Joints. Distinct Endothelial Ligands in Synovium Mediate Leukocyte–subtype Secific Adhesion," *J. Clin. Invest.* 99:2165–2172, American Society for Clinical Investigation (1997).

Salmi, M., et al., "Vascular Adhesion Protein 1 (Vap–1) Mediates Lymphocyte Subtype–specific, Selectin–independent Recognition of Vascular Endothelium in Human Lymph Nodes," *J. Exp. Med.* 186:589–600, Rockefeller University Press (1997).

Salmi, M., et al., "A Cell Surface Amine Oxidase Directly Controls Lymphocyte Migration," *Immunity* 14:265–276, Cell Press (Mar. 2001).

Smith, D.J., et al., "Cloning of Vascular Adhesion Protein 1 Reveals a Novel Multifunctional Adhesion Molecule," *J. Exp. Med.* 188:17–27, Rockefeller University Press (1998).

Takahashi, H., et al., "Synthesis of N–Alkylaminoephedrines and Their Effect on Bronchial Musculature," *Yakugaku Zasshi* 101:1154–1156, Pharmaceutical Society of Japan (1981).

* cited by examiner

INHIBITORS OF COPPER-CONTAINING AMINE OXIDASES

CROSS REFERENCE TO RELATED APPLICATIONS

This application claims the benefit, under 35 U.S.C. §119(e), of the earlier filing date of U.S. Provisional Application No. 60/216,341, filed on Jul. 5, 2000, which is fully incorporated by reference herein.

BACKGROUND OF THE INVENTION

1. Field of the Invention

The present invention is in the field of medicinal chemistry and is directed to hydrazino compounds and their use as inhibitors of copper-containing amine oxidases (E.C. 1.4.3.6) and enzymes of significant identity thereto. The compounds of the present invention have therapeutic utility as drugs to treat diseases including, but not limited to, inflammatory diseases. In particular, acute and chronic inflammatory conditions or diseases such as chronic arthritis, inflammatory bowel diseases and skin dernatoses as well as diseases related to carbohydrate metabolism and to aberrations in adipocyte differentiation or function and smooth muscle cell function may be treated with the compounds.

2. Related Art

VAP-1 is a human endothelial cell adhesion molecule that has several unique properties that distinguish it from the other inflammation-related adhesion molecules. It has a unique and restricted expression pattern and mediates lymphocyte binding to vascular endothelium (Salmi, M., and Jalkanen, S., *Science* 257:1407–1409 (1992)). Inflammation induces the upregulation of VAP-1 to the surface of vascular endothelial cells mediating leukocyte entry to skin, gut and inflamed synovium (Salmi, M., and Jalkanen, S., *Science* 257:1407–1409 (1992); Salmi, M., et al., *J. Exp. Med* 178:2255–2260 (1993); Arvillomi, A., et al, *Eur. J Immunol.* 26:825–833 (1996); Salmi, M., et al., *J. Clin. Invest.* 99:2165–2172 (1997); (Salmi, M., and Jalkanen, S., *J. Exp. Med.* 183:569–579 (1996); *J. Exp. Med.* 186:589–600 (1997)). One of the most interesting features of VAP-1 is a catalytic extracellular domain which contains a monoamine oxidase activity (Smith, D. J., et al., *J. Exp. Med.* 188:17–27 (1998)).

The cloning and sequencing of the human VAP-1 cDNA revealed that it encodes a transmembrane protein with homology to a class of enzymes called the copper-containing amine oxidases (E.C. 1.4.3.6). Enzyme assays have shown that VAP-1 possesses a monoamine oxidase (MAO) activity which is present in the extracellular domain of the protein (Smith, D. J., et al., *J. Exp. Med.* 188:17–27 (1998)). Thus, VAP-1 is an ecto-enzyme. Analysis of the VAP-1 MAO activity showed that VAP-1 belongs to the class of membrane-bound MAO's termed semicarbazide-sensitive amine oxidases (SSAO). These are distinguished from the widely distributed mitochondrial MAO-A and B flavoproteins by amino acid sequence, cofactor, substrate specificity and sensitivity to certain inhibitors. However, certain substrates and inhibitors are common to both SSAO and MAO activities. The mammalian SSAO's can metabolize various monoamines produced endogenously or absorbed as dietary or xenobiotic substances. They act principally on primary aliphatic or aromatic monoamines such as methylamine or benzylamine (Lyles, G. A., *Int. J Biochem. Cell Biol.* 28:259–274 (1996)). Thus, VAP-1 located on the vascular endothelial cell surface can act on circulating primary monoamines with the following reaction pathway.

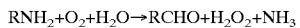

$RNH_2+O_2+H_2O \rightarrow RCHO+H_2O_2+NH_3$

The physiological substrates of VAP-1 SSAO in man have not been clearly identified however methylamine is a good substrate for VAP-1 SSAO. Methylamine is a product of various human biochemical pathways for the degradation of creatinine, sarcosine and adrenaline, and is found in various mammalian tissues and in blood. It can also be derived from the diet by gut bacterial degradation of dietary precursors. The concentration of methylamine in the blood can be increased in certain physiological and pathological situations such as diabetes. Another potential physiological substrates is aminoacetone.

VAP-1 SSAO activity has been proposed to be directly involved in the pathway of leukocyte adhesion to endothelial cells by a novel mechanism involving direct interaction with an amine substrate presented on a VAP-1 ligand expressed on the surface of a leukocyte (Salmi et al. *Immunity*, (2001)). This publication describes the direct involvement of VAP-1 SSAO activity in the process of adhesion of leukocytes to endothelium. Thus inhibitors of VAP-1 SSAO activity could be expected to reduce leukocyte adhesion in areas of inflammation and thereby reduce leukocyte trafficking into the inflamed region and therefore the inflammatory process itself.

In human clinical tissue samples expression of VAP-1 is induced at sites of inflammation. This increased level of VAP-1 can lead to increased production of $H_2O_2$ generated from the action of the VAP-1 SSAO extracellular domain on monoamines present in the blood. This generation of $H_2O_2$ in the localised environment of the endothelial cell could initiate other cellular events. $H_2O_2$ is a known signalling molecule that can upregulate other adhesion molecules and this increased adhesion molecule expression may lead to enhanced leukocyte trafficking into areas in which VAP-1 is expressed. It also may be that other products of the VAP-1 SSAO reaction could have biological effects also contributing to the inflammatory process. Thus the products of the VAP-1 SSAO activity may be involved in an escalation of the inflammatory process which could be blocked by specific SSAO inhibitors.

VAP-1 SSAO may be involved in a number of other pathological conditions associated with an increased level of circulating amine substrates of VAP-1 SSAO. The oxidative deamination of these substrates would lead to an increase in the level of toxic aldehydes and and oxygen radicals in the local environment of the endothelial cell which could damage the cells leading to vascular damage. Increased levels of methylamine and aminoacetone have been reported in patients with Type I and Type II diabetes and it has been proposed that the vasculopathies such as retinopathy, neuropathy and nephropathy seen in late stage diabetes could be treated with specific inhibitors of SSAO activity.

Takahashi, H., et al., *Yakugaku Zasshi* 101(12):1154–1156 (1981), report the synthesis of a number of N-alkylaminoephedrines, including N-(isopropylideneamino)-ephedrine (or R,S-(+)-(2-hydroxy-1-methyl-2-phenylethyl)methylhydrazone-2-propanone):

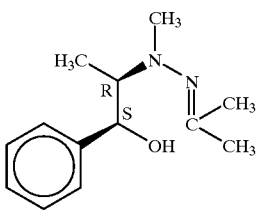

These hydrazone compounds were synthesized to evaluate their effect on the bronchial musculature and were found not to exhibit any significant activity.

Grifantini, M., et al., *Farmaco, Ed. Sci.* 23(3):197–203 (1968), report the synthesis of several alkyl- and acyl-derivatives of N-amino-1-ephedrine and N-amino-d-pseudoephedrine having antidepressant and monoamine oxidase inhibitory properties. Among the compounds disclosed is the hydrazone erythro-(β-hydroxy-α-methylphenethyl) methylhydrazone cyclohexanone, which has the following structure:

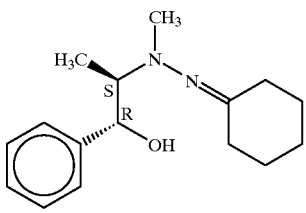

The development of specific VAP-1 SSAO inhibitors that modulate VAP-1 activity would be useful for the treatment of acute and chronic inflammatory conditions or diseases such as chronic arthritis, inflammatory bowel diseases, and skin dermatoses, as well as diseases related to carbohydrate metabolism (including diabetes and complications resulting from diabetes). In addition, aberrations in adipocyte differentiation or function and smooth muscle cell function (in particular, athersclerosis), and various vascular diseases may be suitable for treatment with VAP-1 SSAO inhibitors.

SUMMARY OF THE INVENTION

The present invention is broadly directed to the use of hydrazino compounds of Formula I or II as inhibitors of the class of copper-containing amine oxidases known as semicarbazide-sensitive amine oxidases (SSAO), including the human SSAO known as Vascular Adhesion Protein-1 (VAP-1). As VAP-1 SSAO inhibitors, compounds of the present invention can function to prevent leukocyte adhesion events mediated through SSAO activity as well as other functions of VAP-1 SSAO. Compounds of the present invention are therefore useful for treating a number of inflammatory conditions and diseases of connective tissue, skin, and the gastrointestinal, central nervous system, and pulmonary systems, including such conditions as chronic arthritis, inflammatory bowel diseases, and chronic dermatoses. The compounds are also useful for treating diseases related to carbohydrate metabolism (such as diabetes), to aberrations in adipocyte differentiation or function or smooth muscle cell function (such as atherosclerosis and obesity), and to various vascular diseases (such as atheromatous and nonatheromatous ateriosclerosis, ischemic heart disease, and peripheral aterial occlusion).

A further aspect of the present invention is to provide a pharmaceutical composition useful for treating disorders responsive to a decrease in SSAO activity, containing an effective amount of a compound of Formula I or II in a mixture with one or more pharmaceutically acceptable carriers or diluents.

BRIEF DESCRIPTION OF THE FIGURES

FIGS. 1A–1C depict the inhibition of collagen-induced arthritis in mouse by example compound 9. Control=Vehicle (water), 2029-10=example compound 9 at a dose of 10 mg kg$^{-1}$.

DETAILED DESCRIPTION OF THE INVENTION

Figure 1:
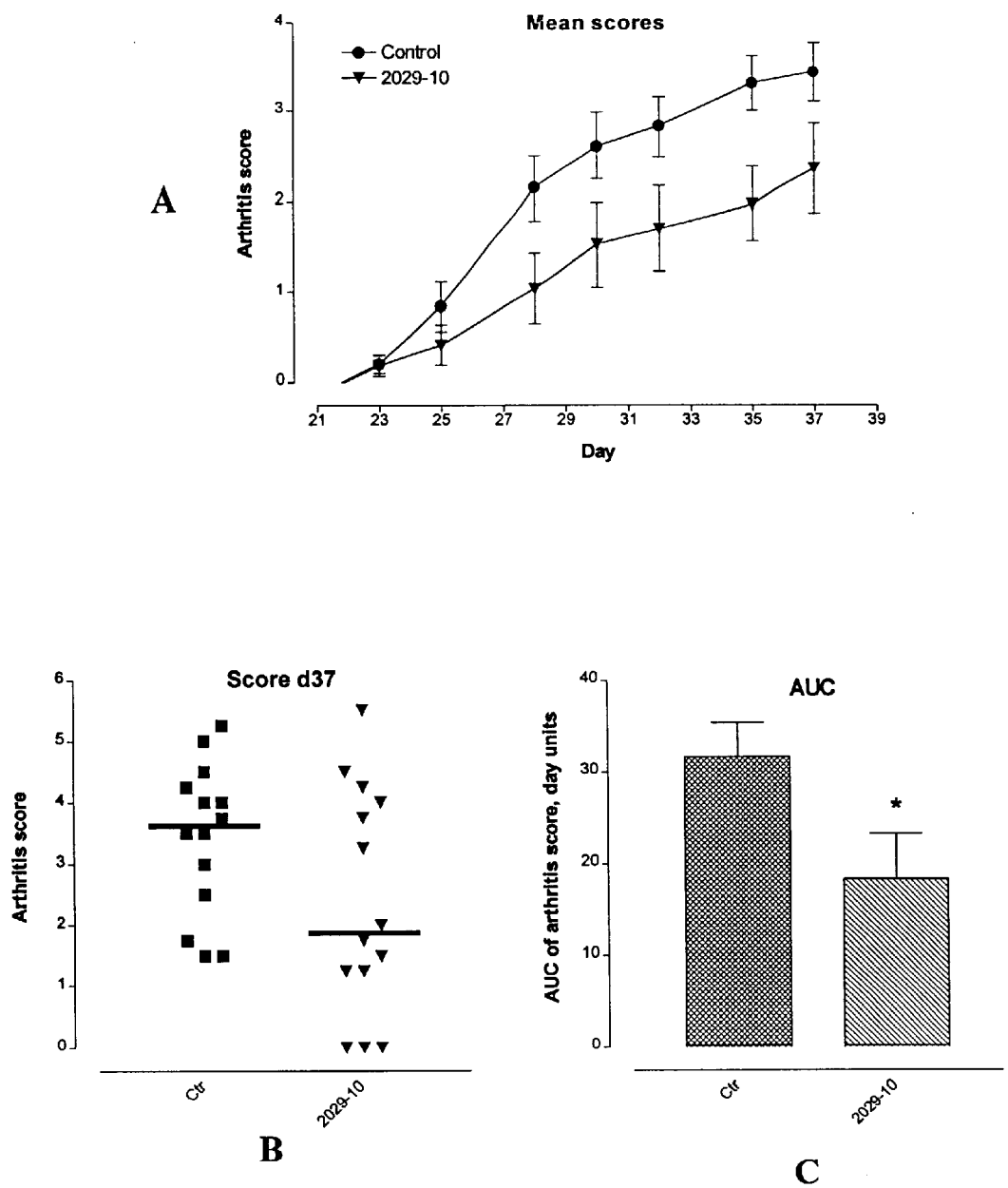
FIG. 1.

One aspect of the invention is to use a specific group of hydrazino compounds having the general formula I or II as defined below, for the manufacture of a pharmaceutical preparation for inhibiting a copper-containing amine oxidase.

Another aspect of the invention is to use a specific group of hydrazino compounds having the general formula I or II as defined below, for the manufacture of a pharmaceutical preparation for the treatment of an inflammatory disease or condition, a disease related to carbohydrate metabolism, a disease related to aberrations in adipocyte differentiation or function or smooth muscle cell function, or a vascular disease.

A further aspect of the present invention is directed to a method of inhibiting a copper-containing amine oxidase, the method comprising contacting said amine oxidase with an inhibitory effective amount of a hydrazino compound of Formula I or II either in racemates or optically pure forms

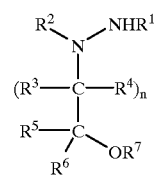

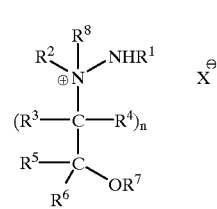

as a racemate or an isomer, or a pharmaceutically acceptable solvate, hydrate, or salt thereof; wherein:

$R^1$ is hydrogen, ($C_1$–$C_4$)alkyl, aralkyl, ($C_2$–$C_5$)alkanoyl, aroyl or heteroaroyl, $R^2$ is hydrogen, or optionally substituted ($C_1$–$C_4$)alkyl, optionally substituted cycloalkyl or optionally substituted aralkyl;

$R^3$–$R^6$, which can be the same or different, are hydrogen, optionally substituted ($C_1$–$C_4$)alkyl, optionally substituted aralkyl, optionally substituted phenyl or optionally substituted heteroaryl;

$R^1$ and $R^2$ can represent an optionally substituted heterocycle, $R^2$ and $R^3$ can represent an optionally substituted heterocycle, $R^3$ and $R^5$ can represent a saturated, optionally substituted carbocycle;

$R^7$ is hydrogen, $(C_1-C_4)$alkyl, $(C_2-C_5)$alkanoyl or aralkyl;

$R^8$ is $(C_1-C_4)$alkyl or aralkyl;

n is 1, 2 or 3;

X is chloride, bromide, iodide or $R^2$-sulfate, wherein $R^2$ has the meaning indicated herein.

In one embodiment, said contacting occurs in vitro. In another embodiment, said contacting occurs in vivo.

The present invention is also directed to methods of treating or preventing inflammatory diseases or conditions using a hydrazino compound of Formula I or II:

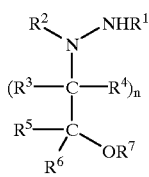

I

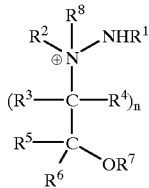

II as a racemate or an isomer, or a pharmaceutically acceptable solvate, hydrate, or salt thereof; wherein:

$R^1$ is hydrogen, or $(C_1-C_4)$alkyl, aralkyl, $(C_2-C_5)$ alkanoyl, aroyl or heteroaroyl $R^2$ is hydrogen, or optionally substituted $(C_1-C_4)$alkyl, optionally substituted cycloalkyl or optionally substituted aralkyl;

$R^3-R^6$, which can be the same or different, are hydrogen, optionally substituted $(C_1-C_4)$alkyl, optionally substituted aralkyl, optionally substituted phenyl or optionally substituted heteroaryl;

$R^1$ and $R^2$ can represent an optionally substituted heterocycle, $R^2$ and $R^3$ can represent an optionally substituted heterocycle, $R^3$ and $R^5$ can represent a saturated, optionally substituted carbocycle;

$R^7$ is hydrogen, $(C_1-C_4)$alkyl, $(C_2-C_5)$alkanoyl or aralkyl;

$R^8$ is $(C_1-C_4)$alkyl or aralkyl;

n is 1, 2 or 3;

X is chloride, bromide, iodide or $R^2$-sulfate, wherein $R^2$ has the meaning indicated herein.

In one embodiment, the hydrazino compounds of Formula I or II are used to treat or prevent connective tissue inflammatory conditions and diseases. In particular, the compounds can be used to treat such conditions or diseases as rheumatoid arthritis, ankylosing spondylitis, psoriatic arthritis, and osteoarthritis.

In another embodiment, the compounds of Formula I or II are used to treat or prevent gastrointestinal inflammatory conditions and diseases, in particular those such as Crohn's disease, ulcerative colitis, and irritable bowel syndrome.

In yet another embodiment, the hydrazino compounds of Formula I or II are used to treat central nervous system inflammatory conditions and diseases, including multiple sclerosis, Alzheimer's disease, and ischaemia-reperfusion injury associated with ischemic stroke.

In another embodiment, the hydrazino compounds of Formula I or II are used to treat or prevent pulmonary inflammatory conditions and diseases. In particular, the compounds can be used to treat or prevent such conditions or diseases as asthma and adult respiratory distress syndrome.

In another embodiment, the hydrazino compounds of Formula I or II are used to treat or prevent chronic inflammatory skin conditions, especially such inflammatory skin conditions as psoriasis, allegic lesions, lichen planus, and pityriasis rosea.

In yet another embodiment, the hydrazino compounds of Formula I or II are used to treat or prevent diseases related to carbohydrate metabolism and complications thereof, such as diabetes and complications from diabetes, microvascular and macrovascular diseases such as atherosclerosis, vascular retinopathies, nephropathies and neuropathies such as polyneuropathy, mononeuropathies, and autonomic neuropathy.

In still another embodiment, the hydrazino compounds of Formula I or II are used to treat or prevent diseases related to or caused by aberrations in adipocyte differentiation or function, such as atherosclerosis or obesity.

In another embodiment, the hydrazino compounds of Formula I or II are used to treat or prevent diseases related to or caused by aberrations in smooth muscle cell function, such as atherosclerosis.

In another embodiment, the hydrazino compounds of Formula I or II are used to treat or prevent vascular diseases, such as atheromatous and nonatheromatous arteriosclerosis, ischemic heart disease, and Raynaud's Disease and Phenomenon.

Preferred compounds are those of Formula I or II wherein n is 1. Also preferred are the compounds wherein $R^1$ is hydrogen, and/or $R^2$ is hydrogen, or $C_1-C_4$ alkyl, or benzyl, any of which may be optionally substituted. Preferred substituents for the benzyl group of $R^2$ are lower alkyl, especially methyl, and nitro, lower alkoxy, especially methoxy and halogen, especially chlorine. Especially preferred embodiments of substituted benzyl groups are p-toluyl, p-nitrobenzyl, p-methoxybenzyl, and p-chlorobenzyl. Suitable values of $R^2$ include hydrogen, methyl, ethyl, propyl, isopropyl, benzyl, p-nitrobenzyl, p-methoxybenzyl, and p-chlorobenzyl. According to an embodiment, alkyl can be substituted with cycloalkyl containing 3 to 9, preferably 3 to 6 carbon atoms.

Preferred compounds of Formula I or II also include those compounds wherein $R^3$, $R^4$, $R^5$ and $R^6$, which can be the same or different, are hydrogen, optionally substituted $C_1$–$C_4$ alkyl, or optionally substituted phenyl, especially when n is 1. Preferred values for $R^3$, $R^4$, $R^5$ and $R^6$ are hydrogen and optionally substituted phenyl. Preferred substituted phenyl groups are those substituted with a lower alkyl, especially methyl, alkoxy, such as methoxy, or a halogen such as chlorine or fluorine. Especially preferred substituted phenyl groups include o-tolyl, m-tolyl, p-tolyl, p-fluorophenyl and p-chlorophenyl.

According to a preferred embodiment, one of $R^5$ and $R^6$ is hydrogen, and the other is optionally substituted phenyl, and n is preferably 1.

Another group of preferred compounds of Formula I or II are those wherein n is 1 and $R^1$ and $R^2$ or $R^2$ and $R^3$ taken together to form an optionally substituted 5–12 membered heterocyclic ring, preferably a 5 to 7 membered single ring or such a ring to which further rings are condensed (i.e., a ring system). Said 5 to 7 membered ring can be either Spiro or fused. The ring can be saturated or comprise double bonds. The ring or ring system can be unsubstituted or substituted, wherein the substituent can be lower alkyl, especially methyl, and nitro, lower alkoxy, especially methoxy and halogen, especially chlorine.

According to one embodiment, n is 1 and $R^3$ and $R^5$ together form a saturated carbocyclic group, which can be substituted as defined for the heterocycles above. Suitable rings include cyclopentane, cyclohexane, 4-methyl-cyclohexane, cycloheptane or a ring included in the adamantane ring system.

In the case where two of the substituents $R^1$, $R^2$, $R^3$ and $R^5$ form a ring, as described above, then it is preferred that the two remaining substituents are hydrogen. When n>1, $R^2$ and $R^3$, or $R^3$ and $R^5$, when forming a ring, are typically on neighbouring carbon atoms. Preferably, when n>1, there is at most one group $R^3$ and/or $R^4$ in the molecule different from hydrogen, such group(s) being preferably adjacent the carbon carrying $R^2$.

$R^1$ and $R^2$ together are preferably saturated heterocycles, e.g. pyrazolidine, hexahydropyridazine and 1,2,3,4-tetrahydrophtalazine.

According to another embodiment n is 1 and the heterocyclic ring formed by the substituents $R^2$ and $R^3$ is a 5 to 6 membered nitrogen containing saturated ring. Said ring can be unsubstituted or substituted. According to a preferred embodiment the substituent is alkyl or alkoxy. According to another embodiment, this 5 to 6 membered nitrogen containing ring can be condensed another ring to form a 1,2,3,4-tetrahydroquinoline, 1,2,3,4-tetrahydroisoquinoline or 2,3-dihydroindole structure. As particularly preferred embodiments can be mentioned piperidine, 1,2,3,4-tetrahydroisoquinoline and 6,7-dimethoxy-1,2,3,4-tetrahydro-isoquinoline.

In the case where $R^2$ and $R^3$ together form a heterocyclic ring, then it is preferred that $R^4$ is hydrogen.

A preferred subgenus of compounds has Formula Ia or IIa:

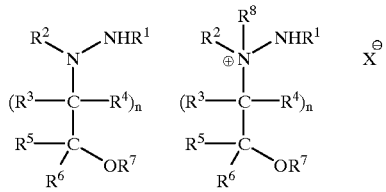

as a racemate or an isomer, or a pharmaceutically acceptable solvate, hydrate, or salt thereof, wherein:

n is 1,
$R^1$ is hydrogen,
$R^2$ is hydrogen, $C_1$–$C_4$ alkyl or phenyl($C_1$–$C_3$)alkyl;
$R^3$ is hydrogen, $C_1$–$C_4$ alkyl or optionally substituted phenyl; or
$R^5$ is hydrogen, $C_1$–$C_4$ alkyl or optionally substituted phenyl; or
$R^3$ and $R^5$ are taken together with the carbon atoms to which they are attached to form a five to seven membered cycloalkyl ring;
$R^4$ and $R^6$ are independently hydrogen or $C_1$–$C_4$ alkyl; and
$R^7$ is hydrogen
$R^8$ is $C_1$–$C_4$ alkyl, and
X is chloride, bromide, iodide.

Examples of compounds of, and useful in, the present invention include:

(1R,2S)-2-(1-Methylhydrazino)-1-phenyl-1-propanol hydrogenmaleate
(1R*,2S*)-2-(1-Methylhydrazino)-1-phenyl-1-propanol hydrochloride
(1R*,2S*)-1-(2-hydroxy-1-methyl-2-phenylethyl)-1,1-dimethylhydrazinium iodide
(1R*,2S*)-2-(1-methylhydrazino)-1,2-diphenylethanol hydrogenmaleate
2-(1-methylhydrazino)-1-phenylethanol hydrogenmaleate
2-(1-methylhydrazino)-2-phenylethanol hydrogenmaleate
1-[2-methoxy-2-(m-methoxyphenyl)ethyl]-1-methylhydrazine hydrogenfumarate
2-Amino-6,7-dimethoxy-1,2,3,4-tetrahydroisoquinoline-1-methanol hydrochloride
2-(1-methylhydrazino)-1-(p-methoxyphenyl)ethanol hydrogenfumarate or a pharmaceutically acceptable salt thereof.

$C_1$–$C_4$ alkyl, as such or as a part of alkoxy or alkanoyl, is a straight or branched alkyl and thus can include methyl, ethyl, n-propyl, isopropyl, n-butyl, sec-butyl, tert-butyl and isobutyl.

The term "aralkyl" as employed herein should be interpreted as any aryl attached to the alkyl, which is a chain of 1 to 6 carbon atoms and which in turn can be straight or branched. Preferably, the chain contains 1 to 3 carbon atoms. Aryl can be an monocyclic or bicyclic aromatic group containing from 6 to 12 carbons in the ring portion, preferably 6–10 carbons in the ring portion, such as phenyl, naphthyl or tetrahydronaphthyl. A preferred aryl group is phenyl, which can be substituted or unsubstituted. Preferable substituents are lower alkyl (i.e., $C_1$–$C_4$ alkyl), especially methyl, or a halogen or lower alkoxy, such as methoxy, or nitro. As particular preferred embodiments can be mentioned benzyl, p-methylbenzyl, p-chlorobenzyl, 2-phenylethyl and 3-phenylpropyl.

The term "($C_2$–$C_5$)-alkanoyl" as employed herein refers to a carbonyl moiety to which is attached an alkyl group, such as any of the above $C_1$–$C_4$ alkyl groups. For example, this term includes, but is not limited to, ethanoyl, propanoyl, butanoyl, 2-methyl propanoyl.

The term "heterocyclic ring" as used herein represents a stable 5- to 7-membered mono- or bicyclic or stable 7- to 12-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, N-benzylpiperidine, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, chromanyl, benzimidazolyl, thiadiazoyl, benzopyranyl, benzothiazolyl, benzo[b]thiophenyl, benzo[2,3-c]1,2,5-oxadiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

A preferred heterocyclic ring is a saturated heterocyclic ring, for example pyrrolidine, piperidine, or 1,2,3,4-tetrahydroisoquinoline, 6,7-dimethoxy-1,2,3,4-tetrahydroisoquinoline, pyrazolidine, tetrahydropyridazine.

The term "heteroaryl" as employed herein refers to groups having 5 to 14 ring atoms; 6, 10 or 14 Π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

Illustrative groups include 2-pyridyl, 3-pyridyl, 4-pyridyl, 2-furyl, 3-furyl, 1-thienyl, 2-thienyl.

The term "heteroaroyl" as emplyed herein refers to a carbonyl moiety attached to a heteroaryl group as defined above.

The term "aroyl" as employed herein refers to a carbonyl moiety attached to an aryl group The term "halogen" or "halo" as employed herein by itself or as part of another group refers to chlorine, bromine, fluorine or iodine.

The term "substituted", unless otherwise provided for herein, refers to one or more groups independently selected from the group consisting of halo, halo ($C_{1-6}$)alkyl, ar($C_{1-6}$)alkyl, aryl, nitro, $C_{1-6}$ alkoxy, and $C_{1-6}$ alkyl as long as the resulting compound is stable. Preferred optional substituents include: halo, ar($C_{1-6}$)alkyl, aryl, and $C_{1-6}$ alkyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

Some of the compounds disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

When any variable occurs more than one time in any constituent or in Formula I or II, its definition on each occurrence is independent of its definition at every other occurrence. Also, combinations of substituents and/or variables are permissible only if such combinations result in stable compounds.

The compounds of the present invention can be prepared by one of the following routes.

Compounds I were synthesized starting from amino alcohols III either via N-nitroso derivatives IV or via oxadiazines V. Nitroso compounds IV were obtained from amino alcohols III in slightly acidic aqueous solution by using sodium nitrite (A. A. Potekhin, A. O. Safronov, *Zhur. Org. Khim.,* 1981, 17, 379–386; H. Takahashi, T. Senda, K. Higashiyama, *Chem. Pharm. Bull.,* 1991, 39, 836–842; J.-K. Shen, H. Katayama, N. Takatsu, I. Shiro, *J. Chem. Soc. Perkin Trans.* 1, 1993, 2087–2097) or by using other well known methods of N-nitrosation (M. A. Zolfigol, M. H. Zebaijadian, G. Chehardoli, H. Keypour, S. Salehzadeh, M. Shamsipur, *J. Org. Chem.,* 2000, 66, 3619–3620). Reductions of nitroso compounds IV were done either in tetrahydrofurane by using lithium aluminium hydride (H. Takahashi, T. Senda, K. Higashiyama, *Chem. Pharm. Bull.,* 1991, 39, 836–842) or in aqueous acetic acid by using zinc dust (D. L. Trepanier, V. Sprancmanis, K. G. Wiggs, *J. Org. Chem.,* 1964, 29, 668–672). Acidic hydrolysis of oxadiazines V ($R^9$ and $R^{10}$ are ($C_1$–$C_4$)alkyl groups or can together represent a 5–7-membered saturated carbocycle), obtained from amino alcohols III and oxaziridines VI (E. Schmitz, S. Schramm, Cs. Szántay, Zs. Kardos, *Liebigs Ann. Chem.,* 1983, 1043–1046), yielded hydrazino alcohols I. Compounds II were obtained by quaternarization of hydrazino alcohols I in acetone or acetonitrile by using alkyl halogenides or sulfates. Compounds I ($R^2$=H) were prepared by the hydrazinolysis of the corresponding oxirane derivatives VII. Regioisomers that formed in the oxirane ring-opening were separated by fractional crystallization, or by chromatography (M. Kim, J. D. White, *J. Am. Chem. Soc.,* 1977, 99, 1172–1180; T. Okawara, S. Ehara, H. Kagotani, Y. Okamoto, M. Eto, K. Harano, T. Yamasaki, M. Furukawa, *J. Org. Chem.,* 1996, 61, 4125–4129; T. Taguchi, J. Ishibashi, T. Matsuo, M. Kojima, *J. Org. Chem.,* 1964, 29, 1097–1103).

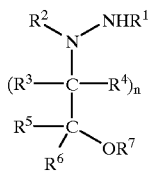

I

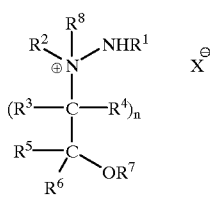

II

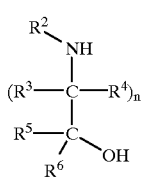

III

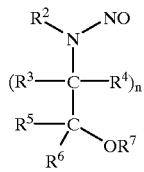

IV

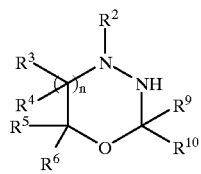

V

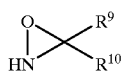

VI

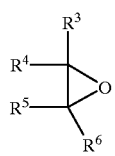

VII

In case of $R^3 \neq R^4$ and $R^5 \neq R^6$, amino alcohols III were used as single diastereomers. The synthesis of the enantiomers of compounds I and II started from enantiomerically pure amino alcohols III or epoxides VII. Transformations occurred without remarkable racemization.

The compounds I of this invention are useful in the form of acid addition salts. The expression "pharmaceutically acceptable acid addition salt" is intended to apply to any non-toxic organic and inorganic acid addition salts of the base compounds of Formula I and II. Illustrative inorganic acids, which form suitable salts include hydrochloric, hydrobromic, sulfuric and phosphoric acids. Illustrative organic acids, which form suitable salts include acetic, lactic, malonic, succinic, glutaric, fumaric, malic, tartaric, citric, ascorbic, maleic, benzoic, phenylacetic, cinnamic, methanesulfonic and salicylic acids.

The present invention provides a method of treating diseases in which VAP-1 has a role by selectively inhibiting VAP-1 SSAO activity, which method comprises administering to an animal in need thereof a therapeutically effective amount of a compound selected from the class of compounds depicted by Formula I or II, wherein one or more compounds of Formula I or II is administered in association with one or more non-toxic, pharmaceutically acceptable carriers and/or diluents and/or adjuvants and if desired other active ingredients.

The compounds of the present invention can be used to treat inflammatory conditions and diseases including but not limited to connective tissue inflammatory conditions and diseases such as ankylosing spondylitis, Reiter's syndrome, psoriatic arthritis, osteoarthritis or degenerative joint disease, rheumatoid arthritis, Sjögren's syndrome, Behçet's syndrome, relapsing polychondritis, systemic lupus erythematosus, discoid lupus erythematosus, systemic sclerosis, eosinophilic fasciitis, polymyositis and dermatomyositis, polymyalgia rheumatica, vasculitis, temporal arteritis, polyarteritis nodosa, Wegener's granulomatosis, mixed connective tissue disease, and juvenile rheumatoid arthritis; gastrointestinal inflammatory conditions and diseases such as Crohn's disease, ulcerative colitis, irritable bowel syndrome (spastic colon), fibrotic conditions of the liver, inflammation of the oral mucosa (stomatitis), and recurrent aphtous stomatitis; central nervous system inflammatory conditions and diseases such as multiple sclerosis, Alzheimer's disease, and ischaemia-reperfusion injury associated with ischemic stroke; pulmonary inflammatory conditions and diseases such as asthma, chronic obstructive pulmonary disease, and adult respiratory distress syndrome; and skin inflammatory conditions and diseases such as contact dermatitis, atopic dermatitis, psoriasis, pityriasis rosea, lichen planus, and pityriasis rubra pilaris.

Moreover, the compounds of the invention can be used to treat diseases related to carbohydrate metabolism and complications thereof, such as diabetes and complications of diabetes including, but not limited to microvascular and macrovascular disease such as atherosclerosis, vascular retinopathies, retinopathy, nephropathy and nephrotic syndrome, neuropathies such as polyneuropathy, mononeuropathies, and autonomic neuropathy, and foot ulcers and joint problems, as well as increased risk of infection; diseases related to or caused by aberrations in adipocyte differentiation or function such as atherosclerosis and obesity; and vascular diseases such as atheromatous and nonatheromatous ateriosclerosis, ischemic heart disease including myocardial infarction, peripheral aterial occlusion, thromboangiitis obliterans (Buerger's disease), and Raynaud's disease and phenomenon.

In particular, the present compounds can be used to treat atherosclerosis. It is known that VAP-1 is expressed on adipocytes, smooth muscle cells, endothelial cells and is related to inflammation. Atherosclerotic plaque consists of accumulated intracellular and extracellular lipids, smooth muscle cells, connective tissue, and glycosaminoglycans. The earliest detectable lesion of atherosclerosis is the fatty streak (consisting of lipid-laden foam cells, which are macrophages that have migrated as monocytes from the circulation into the subendothelial layer of the intima), which later evolves into the fibrous plaque (consisting of intimal smooth muscle cells surrounded by connective tissue and intracellular and extracellular lipids).

The term "treat inflammation" is intended to include the administration of compounds of the present invention to a subject for purposes, which can include prophylaxis, amelioration, prevention or cure of an inflammatory condition or disease. Such treatment need not necessarily completely ameliorate the inflammatory condition or disease. Further, such treatment can be used in conjunction with other traditional treatments for reducing the inflammatory condition known to those of skill in the art.

The compounds of the present invention may be administered in an effective amount within the dosage range of about 0.1 μg/kg to about 300 mg/kg, preferably between 1.0 μg/kg to 10 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid—ethylacrylate copolymers, methacrylic acid—ethyl acrylate copolymers, methacrylic acid—methyl methacrylate copolymers and methacrylic acid—methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

(1R,2S)-2-(1-Methylhydrazino)-1-phenyl-1-propanol hydrogenmaleate (1)

A solution of $NaNO_2$ (1.38 g, 20 mmol) in $H_2O$ (10 ml) was added dropwise to a suspension of (1R,2S)-2-methylamino-1-phenyl-1-propanol hydrochloride (2.02 g, 10 mmol) in $H_2O$ (50 ml) with vigorous stirring on an ice-cold bath, and then AcOH (0.30 g, 5 mmol) was added dropwise. The mixture was stirred at room temperature for 8 h, then was extracted with EtOAc (4×50 ml). The combined organic phases were dried ($Na_2SO_4$) and evaporated under reduced pressure to give 1.86 g N-nitroso derivative as oily product which was used in the next step without farther purification.

A solution of (1R,2S)-2-methylamino-N-nitroso-1-phenyl-1-propanol (1.86 g, 9.6 mmol) in THF (20 ml) was added dropwise to a strirred suspension of $LiAlH_4$ (0.73 g, 19.2 mmol) in THF (50 ml), and the mixture was stirred and refluxed for 3 h. The excess of $LiAlH_4$ was decomposed with a mixture of $H_2O$ (1.5 ml) and THF (20 ml), the resulting precipitate was filtered off and washed with EtOAc (2×75 ml). The combined filtrates were dried (sicc. $Na_2SO_4$) and evaporated under reduced pressure. The semisolid residue was treated with an equivalent amount of maleic acid in a mixture of EtOH and $Et_2O$ to give crystalline hydrogenmaleate salt which was filtered off and recrystallized.

$^1$H-NMR (400 MHz, $D_2O$) δ (ppm): 1.19 (3H, d, J=6.8 Hz, CHCH$_3$), 3.09 (3H, s, NCH$_3$), 3.66 (1H, m, NCH), 5.40 (1H, m, OCH), 6.30 (2H, s, CHCOOH) 7.45 (5H, m, C$_6$H$_5$).

EXAMPLE 2

(1R*,2S*)-2-(1-Methylhydrazino)-1-phenyl-1-propanol hydrochloride (2)

To a solution of 1-oxa-2-azaspiro[2.5]octane (0.60 g, 5.3 mmol) in ether (20 ml) a solution of (1R*,2S*)-2-methylamino-1-phenyl-1-propanol (0.86 g, 5.3 mmol) in ether (5 ml) was added. The reaction mixture was stirred at room temperature for 30 minutes then evaporated to dryness. 5% Hydrochloric acid (30 ml) was added to the residue and the mixture was stirred at ambient temperature for 1 h. The mixture was washed with $Et_2O$ (2×30 ml), made alkaline with $Na_2CO_3$ under ice-cooling and extracted with EtOAc (3×50 ml). The combined EtOAc extracts were dried and evaporated to give a solide residue which was dissolved in methanol (5 ml) and converted to the crystalline hydrochloride salt by using 22% ethanolic hydrogen chloride (2 ml) and diethyl ether. Crystals were filtered off and recrystallized from methanol/diethyl ether.

$^1$H-NMR (400 MHz, $D_2O$) δ (ppm): 1.20 (3H, d, J=6.8 Hz, CHCH$_3$), 3.09 (3H, s, NCH$_3$), 3.67 (1H, m, NCH), 5.41 (1H, br s, OCH), 7.47 (5H, m, C$_6$H$_5$).

EXAMPLE 3

(1R*,2S*)-2-(1-Methylhydrazino)-1-phenyl-1-propanol hydrochloride (2)

To an ice-cooled and stirred suspension of zinc dust (2.62 g, 40 mmol) in $H_2O$ (10 ml) a solution of (1R*,2S*)-2-(1-methylhydrazino)-N-nitroso-1-phenyl-1-propanol (1.94 g, 10 mmol, prepared according to Example 1 starting from (1R*,2S*)-2-methylamino-1-phenyl-1-propanol hydrochloride) in AcOH (18 ml) was added dropwise over a period of 45 min. During the addition, the temperature of the reaction mixture was maintained at 20–25° C. by external cooling. After the addition was completed, the mixture was stirred at 50° C. for 1 h, then filtered by suction, and the zinc residue was washed with a mixture of $H_2O$ (15 ml) and AcOH (5 ml). The combined filtrate and washings were concentrated to ca. 10 ml in vacuo. The iced-cooled solution was made basic with NaOH-solution and extracted with $Et_2O$ (4×50 ml). The combined ethereal extracts were dried and evaporated to give a yellow oil which was dissolved in methanol (5 ml) and converted to the crystalline hydrochloride salt by using 22% ethanolic hydrogen chloride (2 ml) and diethyl ether. Crystals were filtered off and recrystallized from methanol/diethyl ether.

$^1$H-NMR (400 MHz, $D_2O$): see Example 2

EXAMPLE 4

(1R*,2S*)-1-(2-hydroxy-1-methyl-2-phenylethyl)-1,1-dimethylhydrazinium iodide (4)

To a solution of (1R*,2S*)-2-(1-methylhydrazino)-1-phenyl-1-propanol (1.05 g, 5.8 mmol, prepared according to Example 1 starting from (1R*,2S*)-2-methylamino-1-phenyl-1-propanol hydrochloride) in CH$_3$CN (15 ml) MeI (1 ml, 16 mmol) was added. The mixture was left to stand in a closed flask at room temperature for 24 h. The separated crystals were filtered off, washed with CH$_3$CN and recrystallized.

$^1$H-NMR (400 MHz, DMSO-d$_6$) δ (ppm): 1.16 (3H, d, J=6.8 Hz, CHCH$_3$), 3.31 (3H, s, NCH$_3$), 3.32 (3H, s, NCH$_3$), 3.69 (1H, m, NCH), 5.61 (1H, m, OCH), 7.30 (1H, m, C$_6$H$_5$) 7.41 (4H, m, C$_6$H$_5$).

EXAMPLE 5

(1R*,2S*)-2-(1-methylhydrazino)-1,2-diphenylethanol hydrogemnaleate (5)

A solution of NaNO$_2$ (1.38 g, 20 mmol) in H$_2$O (10 ml) was added dropwise to a suspension of (1R*,2S*)-2-(1-methylamino)-1,2-diphenylethanol (2.27 g, 10 mmol) in H$_2$O (30 ml) with vigorous stirring on an ice-cold bath, and then AcOH (0.90 g, 15 mmol) was added dropwise. The mixture was stirred at room temperature for 8 h, then was extracted with EtOAc (4×50 ml). The combined organic phases were dried (Na$_2$SO$_4$) and evaporated under reduced pressure to give 2.04 g crystalline N-nitroso derivative which was used in the next step without further purification.

(1R*,2S*)-2-(1-methylamino)-N-nitroso-1,2-diphenylethanol (2.04 g, 8.0 mmol) was added in small portions to a strirred and ice-cooled suspension of LiAlH$_4$ (0.61 g, 16.1 mmol) in THF (80 ml), and the mixture was stirred at ambient temperature for 3 h. The excess of LiAlH$_4$ was decomposed with a mixture of H$_2$O (1.2 ml) and THF (20 ml), the resulting precipitate was filtered off and washed with EtOAc (2×75 ml). The combined filtrates were dried (sicc. Na$_2$SO$_4$) and evaporated under reduced pressure. The oily product was treated with an equivalent amount of maleic acid in a mixture of EtOH and Et$_2$O to give crystalline hydrogemnaleate salt which was filtered off and recrystallized.

$^1$H-NMR (400 MHz, D$_2$O) δ (ppm): 2.95 (3H, s, NCH$_3$), 4.45 (1H, d, J=5.2 Hz, NCH$_3$), 5.66 (1H, d, J=5.2 Hz, NCH$_3$), 6.30 (2H, s, CHCOOH) 7.15–7.45 (10H, om, 2×C$_6$H$_5$).

EXAMPLE 6

2-(1-methylhydrazino)-1-phenylethanol hydrogenmaleate (6) and 2-(1-methylhydrazino)-2-phenylethanol hydrogenmaleate (6a)

To a stirred solution of hydrazine hydrate (12.5 g, 0.25 mol) in EtOH (10 ml) styrene oxide (3.00 g, 25 mmol) was added dropwise. The exothermic reaction brought the mixture to reflux. After addition was complete, the mixture was kept at 60° C. for 10 min. The solvent was evaporated off and the oily residue was dissolved in EtOH and treated with an equivalent amount of maleic acid. The separated crystals of 2-(1-methylhydrazino)-1-phenylethanol hydrogenmaleate were filtered off and recrystallized from EtOH.

$^1$H-NMR (400 MHz, D$_2$O) δ (ppm): 3.38 (2H, m, NCH$_2$), 5.07 (1H, m, OCH), 6.29 (2H, s, CHCOOH), 7.45 (5H, m, C$_6$H$_5$).

The filtrate was treated with Et$_2$O to give crystalline 2-(1-methylhydrazino)-2-phenylethanol hydrogenmaleate which was filtered off and recrystallized twice from a mixture of EtOH and Et$_2$O.

$^1$H-NMR (400 MHz, D$_2$O) δ (ppm): 3.91 (2H, m, OCH$_2$), 4.32 (1H, m, NCH), 6.30 (2H, s, CHCOOH), 7.47 (5H, m, C$_6$H$_5$).

EXAMPLE 7

1-[2-methoxy-2-(m-methoxyphenyl)ethyl]-1-methylhydrazine Hydrogenfumarate (7)

A solution of NaNO$_2$ (2.81 g, 40.7 mmol) in H$_2$O (10 ml) was added dropwise to a solution of 2-methylamino-1-(m-metoxyphenyl)-1-ethanol hydrochloride (4.39 g, 20.2 mmol) in H$_2$O (20 ml) with vigorous stirring on an ice-cold bath, and then AcOH (2.10 g, 35.0 mmol) was added dropwise. The mixture was stirred at 0° C. for 3 h, kept in refrigerator for 12 h, then diluted with an equal volume of H$_2$O, made alkaline with solid Na$_2$CO$_3$ and extracted with Et$_2$O (3×50 ml). The combined ethereal extracts were dried (Na$_2$SO$_4$) and evaporated under reduced pressure to give 3.53 g yellow viscous oil which was used in the next step without further purification.

55% Sodium hydride suspension (2.00 g, 45.9 mmol) was washed with n-hexane and suspended in THF (50 ml). A solution of 2-methylamino-N-nitroso-1-(m-methoxyphenyl)-1-ethanol (3.00 g, 14.3 mmol) in THF (90 ml) was degassed with N$_2$ flushing and added dropwise to the NaH suspension with stirring and continuous N$_2$ flushing at 0° C. over a period of 1 h. Stirring was continued at 0° C. for 2 h, then a solution of MeI (3.40 g, 24.0 mmol) in THF (30 ml) was added dropwise to the stirred suspension at 0° C. The mixture was allowed to warm to room temperature and the excess of NaH decomposed by addition of MeOH. The solution evaporated to dryness, the residue was dissolved in H$_2$O (50 ml) and extracted with Et$_2$O (3×50 ml). The combined ethereal extracts were washed with H$_2$O (50 ml) then dried (Na$_2$SO4) and evaporated under reduced pressure to give 2.70 g thick yellow oil which was used in the next step without further purification.

A solution of N-methyl-2-methoxy-2-(m-methoxyphenyl)-N-nitroso-ethylamine (2.70 g, 12.0 mmol) in THF (30 ml) was added dropwise to a strirred and ice-cooled suspension of LiAlH$_4$ (1.80 g, 47.4 mmol) in THF (90 ml). The mixture was stirred at 0° C. for 3 h, then allowed to warm to room temperature. The excess of LiAliH$_4$ was decomposed with a mixture of H$_2$O (3.6 ml) and THF (25 ml), the resulting precipitate was filtered off and washed with EtOAc (2×75 ml). The combined filtratee were dried (sicc. Na$_2$SO$_4$) and evaporated under reduced pressure. The oily residue was dissolved in EtOH (20 ml) and mixed with an equivalent amount of fumaric acid dissolved in warm EtOH (25 ml). After cooling the salt separated, filtered off and washed with EtOH.

$^1$H-NMR (400 MHz, DMSO-d$_6$) δ (ppm): 2.44 (3H, s, NCH$_3$), 2.60 (1H, m, NCH$_2$), 2.81 (1H, m, NCH$_2$), 3.14 (3H, s, CHOCH$_3$), 3.75 (3H, s, C$_6$H$_4$OCH$_3$), 4.45 (1H, m OCH), 6.57 (2H, s, CHCOOH), 6.86 (3H, m, C$_6$H$_4$), 7.27 (1H, m, C$_6$H$_4$).

EXAMPLE 8

2-Amino-6,7-dimethoxy-1,2,3,4-tetrahydroisoquinoline-1-methanol hydrochloride (8)

A solution of NaNO$_2$ (1.38 g, 20 nimol) in H$_2$O (10 ml) was added dropwise to a suspension of 6,7-dimethoxy-1,2, 3,4-tetrahydroisoquinoline-1-methanol (2.23 g, 10 mmol) in H$_2$O (50 ml) with vigorous stirring on an ice-cold bath, and then AcOH (0.90 g, 15 mmol) was added dropwise. The mixture was stirred at room temperature for 8 h, then was extracted with EtOAc (4×50 ml). The combined organic phases were dried (Na$_2$SO$_4$) and evaporated under reduced pressure to give 2.37 g crystalline N-nitroso derivative which was used in the next step without further purification.

To a stirred suspension of 6,7-dimethoxy-2-nitroso-1,2,3,4-tetrahydroisoquinoline-1-methanol (2.37 g, 9.4 mmol), zinc dust (2.46 g, 37.6 mmol) and H$_2$O (15 ml) glacial acetic acid (3.00 g, 50 mmol) was added dropwise over a period of 1 h. During the addition, the temperature of the reaction mixture was maintained at 25–30° C. by external cooling. Subsequently the reaction mixture was stirred at 60° C. for 1 h, allowed to cool, and the excess zinc dust filtered by suction and washed with H$_2$O (15 ml). The combined filtrate and washings were made basic with aqueous NaOH-solution and extracted with CHCl$_3$ (4×50 ml). The combined organic phases were dried (sicc. Na$_2$SO$_4$) and evaporated under reduced pressure. The solid residue was dissolved in methanol (5 ml) and converted to the crystalline hydrochloride salt by using 22% ethanolic hydrogen chloride (2 ml) and diethyl ether. Crystals were filtered off and recrystallized from methanol/diethyl ether.

$^1$H-NMR (D$_2$O) δ (ppm): 3.08 (2H, m, CH$_2$CH$_2$N), 3.49 (1H, m, CH$_2$N), 3.76 (1H, m, CH$_2$N), 3.85 (3H, S, OCH$_3$), 3.86 (3H, s, OCH$_3$), 3.94 (1H, m, CH$_2$O), 4.19 (1H, dd, J=12.8, 4.0 Hz, CH$_2$O), 4.47 (1H, m, CHN), 6.93 (1H, S, C$_6$H$_2$), 6.93 (1H, S, C$_6$H$_2$).

EXAMPLE 9

2-(1-methylhydrazino)-1-(p-methoxyphenyl)ethanol hydrogenfumarate (9)

2-methylamino-N-nitroso-1-(p-methoxyphenyl)ethanol (1.15 g, 5.5 mmol, prepared from 2-methylamino-1-(p-methoxyphenyl)ethanol according to Example 1) was added in small portions to a strirred and ice-cooled suspension of LiAlH$_4$ (0.42 g, 11 mmol) in THF (40 ml), and the mixture was stirred at ambient temperature for 2 h. The excess of LiAlH$_4$ was decomposed with a mixture of H$_2$O (0.8 ml) and THF (10 ml), the resulting precipitate was filtered off and washed with EtOAc (3×50 ml). The combined filtrate and washings were dried (sicc. Na$_2$SO$_4$) and evaporated under reduced pressure. The oily product was treated with an equivalent amount of fumaric acid in a mixture of EtOH and Et$_2$O to give crystalline fuimarate salt which was filtered off and recrystallized.

$^1$H-NMR (400 MHz, DMSO-d$_6$) δ (ppm): 2.57 (3H, s, NCH$_3$), 2.74 (2H, m, NCH$_2$), 3.73 (3H, s, OCH$_3$), 4.83 (1H, m, OCH), 6.57 (2H, s, CHCOOH), 6.89 (2H, d, J=8.8 Hz, C$_6$H$_4$), 7.26 (2H, d, J 8.4 Hz, C$_6$H$_4$)

TABLE 1

Physical data of the synthesized racemic compounds

| Number | Structure | M.p. (° C.) | Yield (%) | Formula (M.w.) | Elemental analysis Calcd./Found (%) C | H | N | Synthetic method |
|---|---|---|---|---|---|---|---|---|
| 2 | H$_3$C–CH(N(CH$_3$)NH$_2$·HCl)–C$_6$H$_5$(OH) (R*,S*) | 145–146 | 70 | C$_{10}$H$_{17}$ClN$_2$O (216.71) | 55.42 / 55.61 | 7.91 / 8.04 | 12.93 / 12.86 | Example 1 |
| | | | 57 | | | | | Example 3 |
| 4 | H$_3$C–CH(N$^+$(CH$_3$)$_2$NH$_2$)–C$_6$H$_5$(OH) I$^−$ (R*,S*) | 75–77 | 66 | C$_{11}$H$_{19}$IN$_2$O (322.18) | 41.01 / 40.72 | 5.94 / 6.18 | 8.69 / 8.55 | Example 4 |
| 5 | (C$_6$H$_5$)$_2$CH–CH(N(CH$_3$)NH$_2$)–OH · fumarate (R*,S*) | 152–154 | 71 | C$_{19}$H$_{22}$N$_2$O$_5$ (358.39) | 63.68 / 63.44 | 6.19 / 6.03 | 7.82 / 7.70 | Example 5 |

TABLE 1-continued

Physical data of the synthesized racemic compounds

| Number | Structure | M.p. (° C.) | Yield (%) | Formula (M.w.) | Elemental analysis Calcd./Found (%) C | H | N | Synthetic method |
|---|---|---|---|---|---|---|---|---|
| 6 | 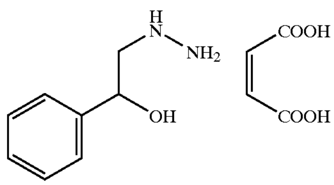 | 120–125 | 48 | $C_{12}H_{16}N_2O_5$ (268.26) | 53.73 53.50 | 6.01 5.83 | 10.44 10.28 | Example 6 |
| 8 | 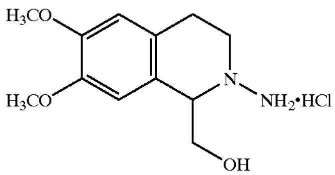 | 210–215 | 67 49 | $C_{12}H_{19}ClN_2O_3$ (274.74) | 52.46 52.13 | 6.97 6.85 | 10.20 10.01 | Example 1 Example 8 |
| 7 | 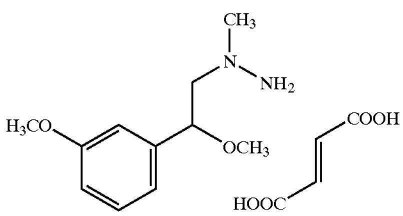 | 139–140 | 52 | $C_{15}H_{22}N_2O_6$ (326.34) | 55.21 55.03 | 6.79 6.45 | 8.58 8.50 | Example 7 |
| 9 | 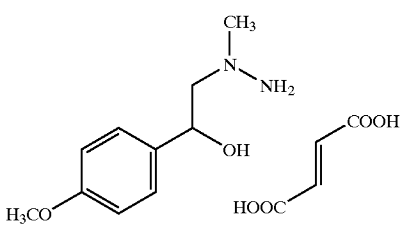 | 142–144 | 67 | $C_{14}H_{20}N_2O_6$ (312.32) | 53.84 53.66 | 6.45 6.30 | 8.97 9.08 | Example 9 |
| 10 | 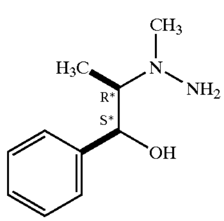 | 78–82 | 72 | $C_{10}H_{16}N_2O$ (180.24) | 66.64 66.28 | 8.95 8.72 | 15.54 15.49 | Example 1 |
| 11 | 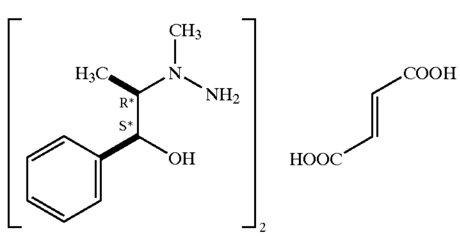 | 141–144 | 74 | $C_{24}H_{36}N_4O_6$ (476.57) | 60.49 60.37 | 7.61 7.44 | 11.76 11.60 | Example 1 |

TABLE 1-continued

Physical data of the synthesized racemic compounds

| Number | Structure | M.p. (° C.) | Yield (%) | Formula (M.w.) | Elemental analysis Calcd./Found (%) | | | Synthetic method |
|---|---|---|---|---|---|---|---|---|
| | | | | | C | H | N | |
| 12 | [structure] | 112–114 | 72 | $C_{14}H_{20}N_2O_5$ (296.32) | 56.75 56.51 | 6.80 6.49 | 9.45 9.26 | Example 1 |
| 13 | [structure] | 98–100 | 68 | $C_{15}H_{22}N_2O_5$ (310.35) | 58.05 57.69 | 7.15 7.03 | 9.03 8.74 | Example 1 |
| 14 | [structure] | 119–122 | 72 55 | $C_{12}H_{21}ClN_2O$ (244.76) | 58.89 59.11 | 8.65 8.54 | 11.45 11.48 | Example 1 Example 3 |
| 15 | [structure] | 133–135 | 70 | $C_{17}H_{24}N_2O_5$ (336.38) | 60.70 60.56 | 7.19 703 | 8.33 8.25 | Example 1 |
| 16 | [structure] | 183–186 | 73 54 | $C_{16}H_{21}ClN_2O$ (292.80) | 65.63 65.31 | 7.23 7.17 | 9.57 9.45 | Example 1 Example 3 |

TABLE 1-continued

Physical data of the synthesized racemic compounds

| Number | Structure | M.p. (°C.) | Yield (%) | Formula (M.w.) | Elemental analysis Calcd./Found (%) C | H | N | Synthetic method |
|---|---|---|---|---|---|---|---|---|
| 17 | (structure) | 160–163 | 75 | $C_{20}H_{24}N_2O_5$ (372.42) | 64.50 / 64.28 | 6.50 / 6.59 | 7.52 / 7.40 | Example 1 |
| 18 | (structure) | 172–174 | 70 | $C_{17}H_{23}ClN_2O_2$ (322.83) | 63.25 / 62.99 | 7.18 / 7.06 | 8.68 / 8.53 | Example 1 |
| 20 | (structure) | 184–186 | 68 | $C_{15}H_{22}N_2O_5$ (310.35) | 58.05 / 57.92 | 7.15 / 6.94 | 9.03 / 8.95 | Example 5 |
| 21 | (structure) | 144–146 | 64 | $C_{15}H_{22}N_2O_5$ (310.35) | 58.05 / 58.31 | 7.15 / 7.04 | 9.03 / 8.97 | Example 1 |
| 22 | (structure) | 170 (decomp.) | 53 | $C_{15}H_{22}N_2O_5$ (310.35) | 58.05 / 57.75 | 7.15 / 6.94 | 9.03 / 8.89 | Example 6 |

TABLE 1-continued

Physical data of the synthesized racemic compounds

| Number | Structure | M.p. (° C.) | Yield (%) | Formula (M.w.) | Elemental analysis Calcd./Found (%) C | H | N | Synthetic method |
|---|---|---|---|---|---|---|---|---|
| 23 | (structure: H₃C-CH₂-CH(R*)-C(S*)(N(CH₃)NH₂)-CH(OH)-phenyl · fumaric acid) | 132–134 | 68 | $C_{16}H_{24}N_2O_5$ (324.37) | 59.24 / 58.97 | 7.46 / 7.38 | 8.64 / 8.49 | Example 1 |
| 24 | (structure: isobutyl-N(CH₃)-N(NH₂)-CH₂-CH(OH)-phenyl · fumaric acid) | 90–92 | 74 | $C_{16}H_{24}N_2O_5$ (324.37) | 59.24 / 59.36 | 7.46 / 7.55 | 8.64 / 8.57 | Example 1 |
| 29 | (structure: 2-chlorophenyl-CH(OH)-CH₂-N(CH₃)-NH₂ · fumaric acid) | 127–128 | 70 | $C_{13}H_{17}ClN_2O_5$ (316.74) | 49.30 / 49.27 | 5.41 / 5.29 | 8.84 / 8.64 | Example 5 |
| 30 | (structure: 4-chlorophenyl-CH(OH)-CH₂-N(CH₃)-NH₂) | 86–88 | 72 | $C_9H_{13}ClN_2O$ (200.66) | 53.87 / 53.61 | 6.53 / 6.48 | 13.96 / 13.87 | Example 5 |
| 33 | (structure: 3-methoxyphenyl-CH(OH)-CH₂-NH-NH₂ · maleic acid) | 130–133 | 49 | $C_{13}H_{18}N_2O_6$ (298.29) | 52.35 / 52.60 | 6.08 / 5.97 | 9.39 / 9.21 | Example 6 |
| 34 | (structure: 3-methoxyphenyl-CH(OH)-CH₂-N(CH₃)-NH₂ · fumaric acid) | 88–90 | 73 | $C_{14}H_{20}N_2O_6$ (312.32) | 53.84 / 53.46 | 6.45 / 6.28 | 8.97 / 8.75 | Example 5 |

TABLE 1-continued

Physical data of the synthesized racemic compounds

| Number | Structure | M.p. (° C.) | Yield (%) | Formula (M.w.) | Elemental analysis Calcd./Found (%) | | | Synthetic method |
|---|---|---|---|---|---|---|---|---|
| | | | | | C | H | N | |
| 35 | (4-methoxyphenyl-CH(OH)-CH2-NH-NH2 · maleic acid) | 117–120 | 47 | $C_{13}H_{18}N_2O_6$ (298.29) | 52.35 52.18 | 6.08 6.13 | 9.39 9.24 | Example 6 |
| 36 | (4-methoxyphenyl-CH(OH)-CH2-NH-NH2 · H3CSO3H) | 135–140 | 49 | $C_{10}H_{18}N_2O_5S$ (278.32) | 43.15 42.96 | 6.52 6.47 | 10.07 9.92 | Example 6 |
| 37 | (4-methoxyphenyl-CH(OCH3)-CH2-N(CH3)-NH2 · fumaric acid) | 104–107 | 54 | $C_{15}H_{22}N_2O_6$ (326.34) | 55.21 55.03 | 6.79 6.84 | 8.58 8.55 | Example 7 |
| 38 | (PhCH2-CH(CH2OH)-N(Bn)-NH2 · maleic acid) | 159–161 | 70 | $C_{20}H_{24}N_2O_5$ (372.42) | 64.50 64.29 | 6.50 6.34 | 7.52 7.48 | Example 5 |
| 41 | (trans-2-(N-benzyl-N-aminoamino)cyclohexanol · HCl) | 217 (subl.) | 72 | $C_{13}H_{21}ClN_2O$ (256.77) | 60.81 60.72 | 8.24 7.93 | 10.91 10.85 | Example 1 |
| 42 | (trans-2-(N-benzyl-N-aminoamino)cyclohexanol) | 108–110 | 76 | $C_{13}H_{20}N_2O$ (220.31) | 70.87 70.63 | 9.15 9.01 | 12.72 12.48 | Example 1 |

TABLE 1-continued

Physical data of the synthesized racemic compounds

| Number | Structure | M.p. (° C.) | Yield (%) | Formula (M.w.) | Elemental analysis Calcd./Found (%) | | | Synthetic method |
|---|---|---|---|---|---|---|---|---|
| | | | | | C | H | N | |
| 43 | [structure: cyclohexane with N(CH$_3$)NH$_2$, OH, phenyl, and HOOC-CH=CH-COOH] | 168–169 | 65 | C$_{17}$H$_{24}$N$_2$O$_5$ (336.38) | 60.70 60.47 | 7.19 6.88 | 8.33 8.14 | Example 1 |
| 45 | [structure: 6,7-dimethoxy tetrahydroisoquinoline with N-NH$_2$·HCl and CH$_2$CH$_2$OH] | 191–192 | 69 55 | C$_{13}$H$_{21}$ClN$_2$O$_3$ (288.77) | 54.07 53.88 | 7.33 7.40 | 9.70 9.67 | Example 1 Example 8 |
| 46 | [structure: tetrahydroisoquinoline with N-NH$_2$·HCl and CH$_2$OH] | 195–197 | 66 | C$_{10}$H$_{15}$ClN$_2$O (214.69) | 55.94 55.63 | 7.04 6.79 | 13.05 12.98 | Example 5 |
| 47 | [structure: 6,7-dimethoxy tetrahydroisoquinoline with N-NH$_2$·HCl and CH$_2$OH] | 246–250 | 71 | C$_{12}$H$_{19}$ClN$_2$O$_3$ (274.74) | 52.46 52.15 | 6.97 6.84 | 10.20 10.15 | Example 5 |

TABLE 2

Physical data of the synthesized enantiomeric compounds

| Number | Structure | M.p. (° C.) | [α]$_D^{20}$ | Yield (%) | Formula (M.w.) | Elemental analysis Calcd./Found (%) | | | Synthetic method |
|---|---|---|---|---|---|---|---|---|---|
| | | | | | | C | H | N | |
| 1 | [structure: H$_3$C-(S)CH-(R)CH(OH)(phenyl)-N(CH$_3$)NH$_2$ with HOOC-CH=CH-COOH] | 111–113 | −36 (MeOH, c = 0.1) | 71 | C$_{14}$H$_{20}$N$_2$O$_5$ (296.32) | 56.75 56.49 | 6.80 6.62 | 9.45 9.37 | Example 1 |

TABLE 2-continued

Physical data of the synthesized enantiomeric compounds

| Number | Structure | M.p. (°C.) | $[\alpha]_D^{20}$ | Yield (%) | Formula (M.w.) | Elemental analysis Calcd./Found (%) | | | Synthetic method |
|---|---|---|---|---|---|---|---|---|---|
| | | | | | | C | H | N | |
| 48 | (structure with CH₃, H₃C, N, NH₂, COOH, OH, phenyl, R/S, COOH) | 112–114 | +32 (MeOH, c = 0.1) | 68 | $C_{14}H_{20}N_2O_5$ (296.32) | 56.75 56.82 | 6.80 6.77 | 9.45 9.40 | Example 1 |
| 49 | (structure with H, N, NH₂, COOH, OH, phenyl, S, COOH) | 99–104 | +43 (MeOH, c = 0.5) | 52 | $C_{12}H_{16}N_2O_5$ (268.26) | 53.73 53.64 | 6.01 5.85 | 10.44 10.38 | Example 6 |
| 50 | (structure with H, N, NH₂, COOH, OH, phenyl, R, COOH) | 98–103 | −44 (MeOH, c = 0.5) | 54 | $C_{12}H_{16}N_2O_5$ (268.26) | 53.73 53.51 | 6.01 5.93 | 10.44 10.28 | Example 6 |

EXAMPLE 10

In Vitro Inhibition of VAP-1 SSAO Activity

VAP-1 SSAO activity was measured using the coupled colourimetric method essentially as described for monoamine oxidase and related enzymes (Holt, A., et al., *Anal. Biochem.* 244:384–392 (1997)). Recombinant human VAP-1 SSAO expressed in Chinese Hamster Ovary (CHO) cells was used as a source of VAP-1 SSAO for activity measurements. Native CHO cells have negligble SSAO activity. These cells and their culture have previously been described (Smith, D. J., et al., *J. Exp. Med.* 188:17–27 (1998)). A cell lysate was prepared by suspending approximately $3.6 \times 10^8$ cells in 25 ml lysis buffer (150 mM NaCl, 10 mM Tris-Base pH 7.2, 1.5 mM $MgCl_2$, 1% NP40) and incubating at 4° C. overnight on a rotating table. The lysate was clarified by centrifugation at 18000 g for 5 min at room temperature and the supernatant used directly in the assay. The VAP-1 SSAO assay was performed in 96 well microtitre plates as follows. To each well was added a predetermined amount of inhibitor if required. The amount of inhibitor varied in each assay but was generally at a final concentration of between 1 nM and 50 µM. Controls lacked inhibitor. The inhibitor was in a total volume of 20 µl in water. The following reagents were then added. 0.2 M potassium phosphate buffer pH 7.6 to a total reaction volume of 200 µl, 45 µl of freshly made chromogenic solution containing 1 mM 2,4-dichlorophenol, 500 µM 4-aminoantipyrine and 4 U/ml horseradish peroxidase and an amount of CHO cell lysate containing VAP-1 SSAO that caused a change of 0.6 $A_{490}$ per h. This was within the linear response range of the assay. The plates were incubated for 30 min at 37° C. and the background absorbance measured at 490 nm using a Wallac Victor II multilabel counter. To initiate the enzyme reaction 20 µl 10 mM benzylamine (final concentration=1 mM) was added and the plate incubated for 1 h at 37° C. The increase in absorbance, reflecting VAP-1 SSAO activity, was measured at 490 nm. Inhibition was presented as percent inhibition compared to control after correcting for background absorbance and $IC_{50}$ values calculated using GraphPad Prism.

EXAMPLE 11

Comparison of VAP-1 SSAO Activity Versus Total Rat MAO Activity

Rat MAO was prepared from rat liver by rinsing the 1 g liver sample several times in 14 ml KCl-EDTA-solution to remove all blood. Then 1 g liver sample was homogenised in 4 ml ice-cold potassium phosphate buffer (0.1 M, pH 7.4) with an Ultra-Turrax homogeniser (setting 11 000 rpm, 4×10 s). After centrifugation at 500 g for 10 min at 4° C. the supernatant was carefully withdrawn and was centrifuged at 12 300 g for 15 min at 4° C. The supernatant was discharged and sedimented mitochondria were resuspended in 4 ml fresh phosphate buffer and centrifuged as previously. The mitochondria were suspended in 4 ml phosphate buffer and homogenized with an Ultra-Turrax homogeniser (setting 11 000 rpm, 2×10 s). Mitochondrial preparate was aliquoted and stored at −70° C. Total MAO activity was measured in a similar way as for VAP-1 SSAO except that 2,4-dichlorophenol was replaced by 1 mM vanillic acid. To each well was added a predetermined amount of inhibitor if required. The amount of inhibitor varied in each assay but was generally at a final concentration of between 10 nM and 800 µM. Controls lacked inhibitor. The inhibitor was in a total volume of 20 µl in water. The following reagents were then added. 0.2 M potassium phosphate buffer pH 7.6 for a total reaction volume of 300 µl, 50 µl of fleshly made chromogenic solution (as above) and 50 µl of MAO preparation. The plates were incubated for 30 min at 37° C. and the background absorbance measured at 490 nm using a Wallac Victor II multilabel counter. To initiate the enzyme reaction 20 µl of 5 mM tyramine (final concentration 0.5 mM) was added and the plate incubated for 1 h at 37° C. The increase in absorbance, reflecting MAO activity, was measured at 490 um. Inhibition was presented as percent inhibition compared to control after correcting for background absorbance and $IC_{50}$ values calculated using GraphPad Prism. Clorgyline and pargyline (inhibitors of MAO-A and -B respectively) at 0.5 µM were added to some wells as positive controls for MAO inhibition.

The ability of compounds of Examples 1 to 9 to inhibit VAP-1 SSAO activity with specificity for VAP-1 SSAO over rat MAO is shown in Table 3. The results indicate that the compounds of the invention are specific inhibitors of human VAP-1 SSAO activity. The compounds of the present invention are therefore expected to have therapeutic utility in the treatment of diseases and conditions in which the SSAO activity of the human adhesion molecule VAP-1 plays a role.

TABLE 3

Potency and specificity of Examples 1 to 9

| Example Compound | VAP-1 SSAO inhibitory activity $IC_{50}$ µM | Total MAO inhibitory activity $IC_{50}$ µM | Selectivity for VAP-1 SSAO over MAO |
|---|---|---|---|
| 4 | >50 | >500 | ≈10 |
| 2 | 0.35 | 39 | 111 |
| 5 | 0.41 | 54 | 132 |
| 6 | 0.065 | 8.90 | 137 |
| 7 | 0.41 | 44 | 107 |
| 1 | 0.22 | 31 | 141 |
| 8 | >10 | 78 | <8 |
| 9 | 0.31 | 36 | 116 |
| 10 | 0.30 | 36 | 120 |
| 11 | 0.17 | 16 | 94 |
| 12 | 0.29 | 40 | 138 |
| 13 | 1.52 | 25 | 16 |
| 14 | 129 | >800 | >6 |
| 15 | 1.38 | 10 | 7 |
| 16 | 4.00 | 249 | 62 |
| 17 | 34 | 231 | 6 |
| 18 | 2.60 | 22 | 9 |
| 20 | 0.52 | 55 | 98 |
| 21 | 0.26 | 41 | 158 |
| 22 | 1.20 | 11 | 9 |
| 23 | 0.26 | 28 | 108 |
| 24 | 0.35 | 11 | 32 |
| 29 | 0.27 | 23 | 85 |
| 30 | 0.31 | 21 | 68 |
| 33 | 0.052 | 9.10 | 175 |
| 34 | 0.28 | 44 | 157 |
| 35 | 0.029 | 6.00 | 207 |
| 36 | 0.017 | 5.00 | 294 |
| 37 | 0.42 | 44 | 105 |
| 38 | >50 | >500 | ≈10 |
| 41 | 21.9 | 111 | 5 |
| 42 | 3.70 | 106 | 29 |
| 43 | 0.52 | 10.0 | 19 |
| 45 | 8.10 | 45 | 6 |

TABLE 3-continued

Potency and specificity of Examples 1 to 9

| Example Compound | VAP-1 SSAO inhibitory activity $IC_{50}$ µM | Total MAO inhibitory activity $IC_{50}$ µM | Selectivity for VAP-1 SSAO over MAO |
|---|---|---|---|
| 46 | >10 | 614 | <61 |
| 47 | >10 | 1500 | <150 |
| 48 | 0.28 | 31 | 110 |
| 49 | 0.14 | 9.80 | 70 |
| 50 | 0.035 | 9.90 | 283 |

EXAMPLE 12

Inhibition of Collagen-induced Arthritis in Mouse
The Model in the Literature

Mouse collagen-induced arthritis (CIA) is a frequently used model both for studying the basic mechanisms of autoimmune arthritis and in assessing the efficacy of potential antiarthritic agents (van den Berg and Joosten, 1999 in In Vivo Models of Inflammation (Morgan D W and Marshall L A eds) pp 51–75, Birkhauser Verlag, Basel). Compounds acting through various mechanisms have been demonstratd to be effective in the model and they include cyclooxygenase inhibitors, interleukins 4 and 10, leukotriene synthesis inbitors and anti-TNF antibodies (Joosten et al., *J. Immunol.* 159:4094–4102. 1997; van den Berg and Joosten, 1999 in In Vivo Models of Inflammation (Morgan D W and Marshall L A eds) pp 51–75, Birkhauser Verlag, Basel)).
Description of the Model Used The study was conducted with groups of 14 mice to obtain statistically valid results. For arthritis induction DBA/1 mice (male, aged 10–12 weeks, approximate weight 25 g) were immunized with bovine type II collagen (100 µg) emulsified in Freund's complete adjuvant by four subcutaneous injections in the back. At day 21, animals were boosted with an i.p. injection of 100 µg collagen type II diluted in PBS. This strain is highly susceptible to CIA induced with bovine type II collagen. After the second immunization, polyarthritis starts to develop in 1 to 2 weeks, with a disease incidence of approx. 80% at day 38 (Joosten et al., *J. Immunol.* 159:4094–4102. 1997). Arthritis development was scored from day 21 onwards. Animals were treated for 2.5 weeks starting after the second booster but before the arthritis onset (day 23). Intraperitoneal medication with example compound 9 (10 mg $kg^{-1}$ twice daily) was initiated at day 23 and continued until day 37.
Outcome A reduction in the cumulative score (p<0.05 by Dunn's test following Kruskal-Wallis test) was detected.

Having now filly described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method of inhibiting a human semicarbazide-sensitive amine oxidase (SSAO), comprising contacting said amine oxidase with an inhibitory amount of a hydrazino compound of Formula I or Formula II:

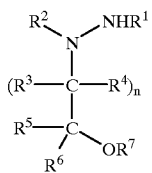

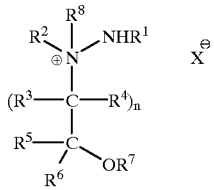

or a stereoisomer or pharmaceutically acceptable solvate, hydrate, or salt thereof; wherein:

$R^1$ is hydrogen, $(C_1-C_4)$alkyl, aralkyl, $(C_2-C_5)$alkanoyl, aroyl or heteroaroyl;

$R^2$ is hydrogen, or optionally substituted $(C_1-C_4)$alkyl, optionally substituted cycloalkyl or optionally substituted aralkyl;

$R^3-R^6$, which can be the same or different, are hydrogen, optionally substituted $(C_1-C_4)$alkyl, optionally substituted aralkyl, optionally substituted phenyl or optionally substituted heteroaryl;

or $R^1$ and $R^2$, together with the atoms to which they are attached, represent an optionally substituted heterocycle, or $R^2$ and $R^3$, together with the atoms to which they are attached, represent an optionally substituted heterocycle, or $R^3$ and $R^5$, together with the atoms to which they are attached, represent a saturated, optionally substituted carbocycle;

$R^7$ is hydrogen, $(C_1-C_4)$alkyl, $(C_2-C_5)$alkanoyl or aralkyl;

$R^8$ is $(C_1-C_4)$alkyl or aralkyl;

n is 1, 2 or 3; and

X is chloride, bromide, iodide or $R^2$-sulfate, where $R^2$ is as defined herein.

2. The method of claim 1, wherein said contacting occurs in vitro.

3. The method of claim 1, wherein said contacting occurs in vivo.

4. The method of claim 1, wherein n is 1.

5. The method of claim 1, wherein $R^1$ is hydrogen.

6. The method of claim 1, wherein $R^2$ is benzyl optionally substituted with alkyl, nitro, methoxy, or halogen.

7. The method of claim 1, wherein $R^6$ is phenyl optionally substituted with alkyl, nitro, methoxy, or halogen, and $R^5$ is hydrogen.

8. The method claim 1, wherein n is 1, and $R^3$ and $R^5$ together form a cyclohexane ring.

9. The method of claim 1, wherein n is 1, $R^4$ is hydrogen, and $R^2$ and $R^3$ are taken together with the atoms to which they are attached to form an optionally substituted heterocyclic ring selected from the group consisting of pyrrolidine, piperidine, tetrahydroisoquinoline, and pyrazolidine, wherein said heterocyclic ring is optionally substituted with alkyl, nitro, methoxy, or halogen.

10. The method of claim 1, wherein n is 1, and $R^3$ and $R^4$, which can be the same or different, are $(C_1-C_4)$alkyl.

11. The method of claim 1, wherein $R_3-R^6$, which can be the same or different, are optionally substituted $(C_1-C_4)$ alkyl, optionally substituted aralkyl, optionally substituted phenyl or optionally substituted heteroaryl.

12. The method of claim 1, wherein $R^2$ is p-toluyl, p-nitrobenzyl, p-methoxybenzyl, p-chlorobenzyl, methyl, ethyl, propyl, isopropyl, or benzyl.

13. The method of claim 1, wherein n is 1 and one of $R^5$ and $R^6$ is hydrogen and the other is optionally substituted phenyl.

14. The method of claim 1, wherein $R^3$, $R^4$, $R^5$, and $R^6$, which can be the same or different, are hydrogen or optionally substituted phenyl.

15. The method of claim 1, wherein:

n is 1;

$R^1$ is hydrogen;

$R^2$ is hydrogen, $(C_1-C_4)$ alkyl or phenyl$(C_1-C_3)$alkyl;

$R^3$ is hydrogen, $(C_1-C_4)$ alkyl or optionally substituted phenyl;

or $R^5$ is hydrogen, $(C_1-C_4)$ alkyl or optionally substituted phenyl;

or $R^3$ and $R^5$ taken together with the carbon atoms to which they are attached form a 5–7 membered cycloalkyl ring;

$R^4$ and $R^6$ are independently hydrogen or $(C_1-C_4)$ alkyl;

$R^7$ is hydrogen;

$R^8$ is $(C_1-C_4)$ alkyl; and

X is chloride, bromide, or iodide.

* * * * *